United States Patent
Pelipenko et al.

(10) Patent No.: US 10,702,477 B2
(45) Date of Patent: Jul. 7, 2020

(54) AFATINIB-CONTAINING FORMULATION

(71) Applicant: Sandoz AG, Basel (CH)

(72) Inventors: Jan Pelipenko, Ljubljana (SI); Katja Kristan, Ljubljana (SI); Marko Oblak, Ljubljana (SI); Miha Homar, Ljubljana (SI); Rok Grahek, Ljubljana (SI)

(*) Notice: Subject to any disclaimer, the term of this patent is extended or adjusted under 35 U.S.C. 154(b) by 0 days.

(21) Appl. No.: 16/066,347

(22) PCT Filed: Oct. 11, 2016

(86) PCT No.: PCT/EP2016/074299
§ 371 (c)(1),
(2) Date: Jun. 27, 2018

(87) PCT Pub. No.: WO2017/064039
PCT Pub. Date: Apr. 20, 2017

(65) Prior Publication Data
US 2019/0029962 A1    Jan. 31, 2019

(30) Foreign Application Priority Data

Oct. 12, 2015 (EP) .................................. 15189380

(51) Int. Cl.
*A61K 9/16* (2006.01)
*A61K 31/517* (2006.01)
(Continued)

(52) U.S. Cl.
CPC ............ *A61K 9/1682* (2013.01); *A61K 9/146* (2013.01); *A61K 9/1611* (2013.01);
(Continued)

(58) Field of Classification Search
CPC .. A61K 9/11682; A61K 9/2095; A61K 9/146; A61K 9/1694; A61K 9/1676;
(Continued)

(56) References Cited

U.S. PATENT DOCUMENTS 8,545,884 B2    10/2013  Messerschmid et al.
2015/0110871 A1*  4/2015  Wong .................. A61K 9/0065
                                                      424/469

FOREIGN PATENT DOCUMENTS

WO    2009147238 A1    12/2009
WO    2017033107 A1 *   3/2017

OTHER PUBLICATIONS https://www.google.com/url?sa=t&rct=j&q=&esrc=s&source=web&cd=3&cad=rja&uact=8&ved=2ahUKEwjB48mF9fjiAhXFm-AKHQ-KAb8QFjACegQIBBAB&url=https%3A%2F%2Fwww.rxlist.com%2Fgilotrif-drug.htm&usg=AOvVaw3xAFagPy6ZXwaC5_J4Hkjh, 2019.*

(Continued)

*Primary Examiner* — Carlos A Azpuru
(74) *Attorney, Agent, or Firm* — Luedeka Neely Group, P.C.

(57) ABSTRACT

The present invention refers to a process for preparing granules or particles comprising afatinib dimaleate, comprising the steps of providing afatinib dimaleate and at least one pharmaceutically acceptable excipient, and preparing granules or particles involving the use of at least one solvent selected from organic solvent and water, wherein all pharmaceutically acceptable excipients used in the process for preparing granules or particles have neutral or acidic properties, and wherein afatinib dimaleate has a solubility of at least 5 mg/ml in said at least one solvent. The present invention further refers to granules or particles comprising afatinib dimaleate that are prepared according to this process. Additionally, the present invention refers to a process for preparing a pharmaceutical composition comprising afatinib dimaleate, as well as to an adsorbate comprising afatinib dimaleate. Finally, the present invention refers to a (Continued)

pharmaceutical composition comprising afatinib dimaleate for use in a method of treating certain diseases.

16 Claims, 1 Drawing Sheet

(51) Int. Cl.
*A61K 9/20* (2006.01)
*A61K 9/14* (2006.01)

(52) U.S. Cl.
CPC .......... *A61K 9/1635* (2013.01); *A61K 9/1676* (2013.01); *A61K 9/1694* (2013.01); *A61K 9/2009* (2013.01); *A61K 9/2018* (2013.01); *A61K 9/2095* (2013.01); *A61K 31/517* (2013.01)

(58) Field of Classification Search
CPC .. A61K 9/1635; A61K 9/1611; A61K 9/2009; A61K 31/517; A61K 9/1682
See application file for complete search history.

(56) References Cited

OTHER PUBLICATIONS

International Preliminary Report on Patentability for PCT/EP2016/074299, dated Apr. 17, 2017, 7 pages.
International Search Report and Written Opinion for PCT/EP2016/074299, dated Apr. 20, 2018, 10 pages.

\* cited by examiner

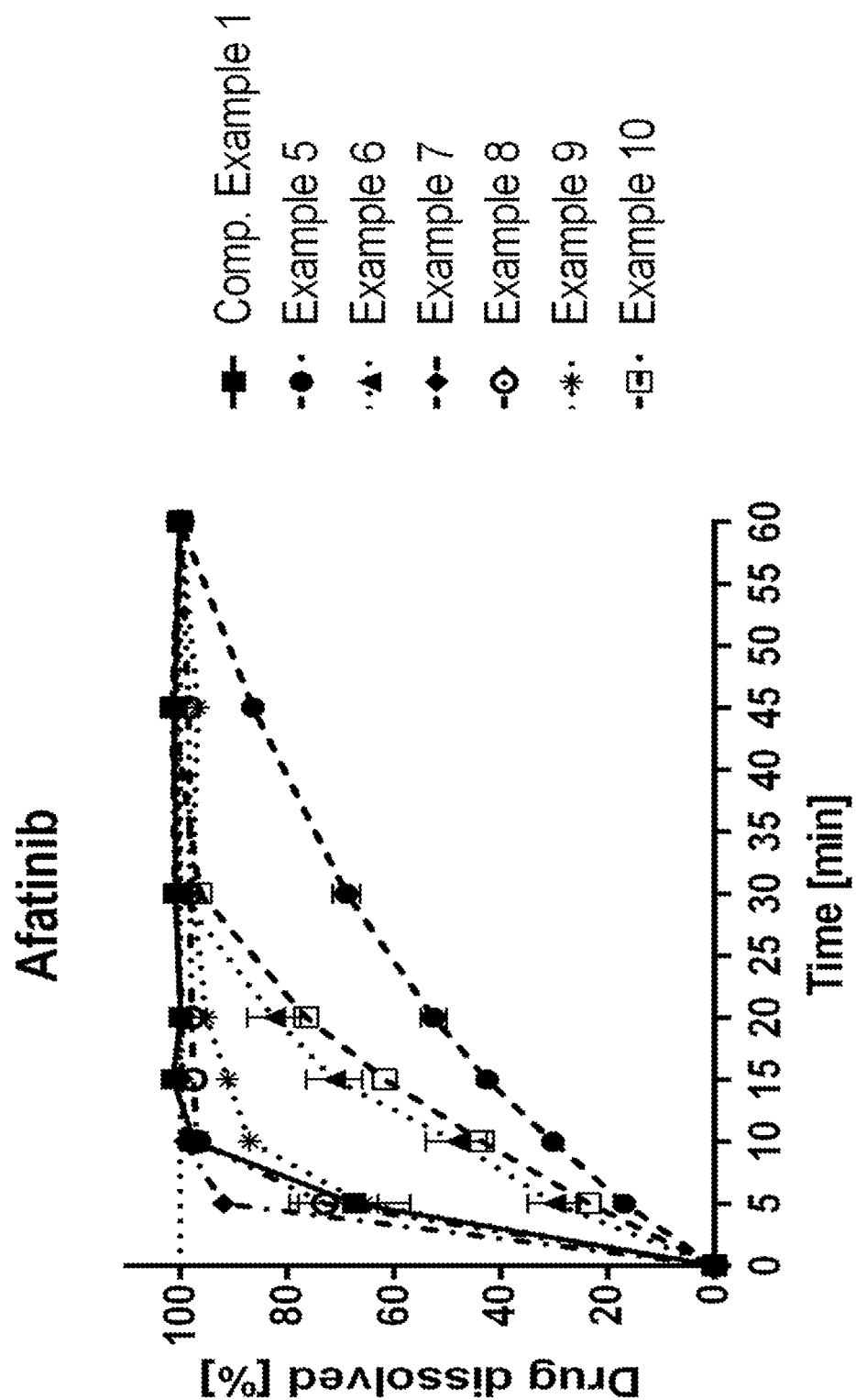

AFATINIB-CONTAINING FORMULATION

This application is a Section 371 national phase entry of PCT application PCT/EP2016/074299, filed Oct. 11, 2016. This application also claims the benefit of the earlier filing date of European patent application 15189380.7, filed Oct. 12, 2015.

FIELD OF THE INVENTION

The present invention belongs to the field of pharmaceutical industry and relates to a process for preparing granules or particles comprising afatinib dimaleate, and to a process for preparing pharmaceutical compositions comprising said granules or particles. Furthermore, the invention refers to the granules or particles itself, as well as to pharmaceutical compositions comprising said granules or particles, and the use thereof for treating specific diseases.

DESCRIPTION OF THE BACKGROUND ART

It is well known in the art that pharmaceutically active ingredients (APIs) exhibit a wide variety of physicochemical characteristics that influence and that are relevant for e.g. the handling of the API, such as its manufacture. When manufacturing API, e.g. into final dosage forms, it is important that, on the one hand, adequate formulation characteristics are achieved, and on the other hand, that the intermediates of such formulations or final dosage forms can be adequately processed, such as in a robust, fast, and cost efficient way.

The respective physicochemical characteristics influence the segregation of the API inside the powder mixture during its movement e.g. in pipes, hopper and/or feeder of apparatus used for processing the API. Further, these characteristics influence reproducibility and content uniformity of the API in a batch or between batches, in particular in low dose formulations or direct compression processes. Also, parameters such as flowability, compressibility, cohesiveness and lubrication of the API or mixtures of API and excipients are influenced by the specific characteristics of an API and thus may be critical as to processibility in automated production.

Thus, in order to improve properties of the API which are relevant to the manufacturing process, various ways of processing the API are known in prior art. For instance, prior to incorporation of the API into a pharmaceutical formulation, the API can be subjected to several physical or physicochemical processes such as recrystallization, transformation into different polymorphic forms or transformation of the API into intermediate forms, such as solid forms like granules or particles, which may then be further processed. Processes an API can be subjected to may be the conversion of powders comprising the API to granules or particles. The conversion of powders to granules is called "granulation". The most commonly employed granulation methods are wet-granulation, dry granulation and hot-melt granulation. The thus-obtained granules or particles can then be further processed, e.g. into dosage forms such as solid oral dosage forms.

Amongst other factors, also the respective susceptibilities of an API e.g. towards certain solvents or treatments have to be taken into account when processing it. An example of an API that is known to have challenging physical and physicochemical properties that are relevant with regard to the processibility is afatinib dimaleate: It exhibits susceptibility against moisture affecting the chemical stability of the API; the precipitated API exhibits a needle shape, causing a high variation of its poured density due to random arrangement and length of the needles; it exhibits poor flow properties due to increased resistance of the needles to align in flow direction; capping or laminating of tablets can occur during a direct compression process due to entrapment of too much air inside the final blend; it exhibits a low compressibility; it exhibits adhesive properties on surfaces; and/or finally it exhibits a random variability of its poured densities.

U.S. Pat. No. 8,545,884 B2 discloses a process comprising a step of compacting the API afatinib dimaleate for densification, followed by a sieving step, in order to provide API that is suitable for further processing.

Despite the above described process steps, there is still a need and thus an object for improved methods for preparing granules or particles comprising afatinib dimaleate, for improved granules or particles, as well as for improved dosage forms comprising said granules or particles.

SUMMARY OF THE INVENTION

The present invention provides the following aspects, subject-matters and preferred embodiments, which respectively taken alone or in combination, contribute to solving the object of the present invention:

1. Process for preparing granules or particles comprising afatinib dimaleate, wherein the process comprises:
   (a) providing afatinib dimaleate and at least one pharmaceutically acceptable excipient; and
   (b) preparing granules or particles by use of afatinib dimaleate and at least one pharmaceutically acceptable excipient as provided in step (a), and at least one solvent selected from organic solvents and water;
   wherein all pharmaceutically acceptable excipients which are used in the process for preparing granules or particles have neutral or acidic properties,
   wherein the excipient is determined to have neutral properties if the pH of a solution/suspension of the excipient in water when measured by pH meter has a pH of 6 to 8, and wherein the excipient is determined to have acidic properties if the pH of the solution/suspension of the excipient in water has a pH of less than 6,
   and wherein said afatinib dimaleate as provided in step (a) has a solubility of at least 5 mg/ml in said at least one solvent of step (b).

2. The process according to the preceding item, wherein the at least one solvent is an organic solvent, preferably the organic solvent is selected from the group consisting of acetone, methanol, ethanol, and 2-propanol; more preferably, the organic solvent is acetone and/or methanol.
   It is also possible that the organic solvent is a mixture of organic solvents, or of organic solvents and water.

3. The process according to the preceding items, wherein the at least one excipient used has acidic properties. Typically, at least a binder and/or carrier is used.

4. The process of any of the preceding items, which is selected from the group consisting of wet granulation (e.g. fluid bed granulation), spray-coating, spray-drying and adsorbate formation, preferably the process is selected from the group consisting of wet granulation, spray-drying, and adsorbate formation.

5. The process according to the preceding item, wherein, if the process is wet granulation, afatinib dimaleate has a solubility of at least 20 mg/ml in the at least one solvent used, preferably at least 25 mg/ml; if the process is adsorbate formation, the afatinib dimaleate has a solubility of at least 5 mg/ml in the at least one solvent used, preferably at least 8 mg/ml; if the process is spray drying, the afatinib dimaleate has a solubility of at least 5 mg/ml in the at least one solvent used, preferably at least 8 mg/ml; and if the process is spray-coating, the afatinib dimaleate has a solubility of at least 5 mg/ml. preferably at least 8 mg/ml.

6. The process according to any of the preceding items, comprising the use of at least one carrier, wherein said at least one carrier has neutral or acidic properties, preferably acidic properties, as determined by the method indicated in item 1.

7. The process according to any of the preceding items, wherein the at least one carrier with neutral or acidic properties is selected from the group consisting of lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate, magnesium aluminum silicates, silica, dextrose, silicon dioxide, croscarmellose sodium, sodium starch glycolate, and crospovidone; preferably the at least one carrier is selected from the group consisting of silicon dioxide, croscarmellose sodium, sodium starch glycolate, and crospovidone.

8. The process according to any of the preceding items, wherein the granules or particles of step b) additionally comprise an antioxidant, preferably this antioxidant is selected from the group consisting of butylated hydroxytoluene, butylated hydroxyanisole, alpha tocopherol, rosmarinic acid, monothioglycerol, thioglycolic acid, ascorbic acid, dodecyl gallate, propyl gallate, octyl gallate, sodium ascorbate, sodium metabisulfite sodium sulfite, sodium bisulfite; more preferably the antioxidant is butylated hydroxytoluene (BHT).

9. The process according to any of the preceding items, which is a wet granulation process for preparing granules comprising afatinib dimaleate, wherein a granulation liquid comprising the at least one solvent, preferably methanol or water, and at least one binder, is used.

10. The process of item 9, wherein afatinib dimaleate is completely dissolved in the granulation liquid.

11. The process according to item 9 or 10, wherein the at least one binder is selected from the group consisting of: polymeric cellulose derivatives, such as carboxymethyl cellulose (CMC), hydroxypropyl cellulose (HPC), hydroxyethyl cellulose (HEC) and hydroxypropylmethyl cellulose (HPMC); gelatin; gelatin hydrolysate; sucrose; dextrose; and non-cellulosic binders, such as polyvinylpyrrolidone (PVP), polyethyleneglycol (PEG), vinyl pyrrolidone copolymers, pregelatinized starch, sorbitol, and glucose; and polyacrylates (e.g. Eudragit®); preferably the at least one binder is selected from the group consisting of: polyvinylpyrrolidone and its derivatives such as Kollidon; cellulose derivatives such as HPMC; and polyoxyethylene/polyethyleneglycol polymers such as PEG; more preferably the at least one binder is selected from the group consisting of Kollidon, HPMC and PEG 6000.

12. The process according to item 11, wherein the at least one binder is selected from polyvinylpyrrolidone and its derivatives, such as Kollidon VA64®; cellulose derivatives, such as HPMC; and polyoxyethylene/polyethyleneglycol polymers (e.g. PEG 6000), and/or wherein lactose, sodium starch glycolate or silica (silicon dioxide) is used as a carrier.

13. The process according to item 1 to 4, 8, 11 or 12, which is a spray-drying process for preparing granules comprising afatinib dimaleate, wherein a solution comprising afatinib dimaleate, the at least one solvent and optionally at least one binder is subjected to a spray-drying process, wherein preferably polyvinylpyrrolidone and/or its derivatives, such as Kollidon VA64®, are used as binder.

14. The process according to any of the preceding items, wherein afatinib dimaleate is present in the granules or particles in amorphous or crystalline form, preferably in amorphous form.

15. The process according to any of items 1-8, which is a process for preparing an adsorbate comprising afatinib dimaleate on a carrier, comprising:
i) combining a solution comprising afatinib dimaleate and the at least one solvent with the at least one carrier;
ii) removing the solvent or mixture of solvents under reduced pressure to form the adsorbate.

16. The process according to item 15, wherein the pressure applied in step ii) is from 1 to 350 mBar, preferably from 20 to 250 mBar.

17. The process according to item 15 or 16, wherein the carrier is silica, and/or wherein the solvent is acetone.

18. The process according to any of the preceding items, wherein the process is carried out in the absence of pharmaceutically active ingredients other than afatinib dimaleate.

The granules or particles that are obtained by applying the process as disclosed herein can be further processed, for instance they can be used in preparing pharmaceutical compositions. In this case, the granules or particles do not represent a final dosage form, but rather an intermediate.

19. Process for preparing a pharmaceutical composition comprising afatinib dimaleate, comprising the steps of:
(A) carrying out a process according to any of items 1 to 18;
(B) mixing the prepared granules or particles comprising afatinib dimaleate with one or more additional pharmaceutically acceptable excipients.

20. The process according to item 19, wherein said one or more additional pharmaceutically acceptable excipient is selected from the group consisting of fillers, disintegrants, binders, lubricants, glidants, surfactants, wetting agents, film-forming agents and coating materials, sweeteners, flavoring agents, and coloring agents.

21. Granules or particles comprising afatinib dimaleate, wherein the granules or particles are prepared by a process as defined in any of items 1-18.

22. The granules or particles according to item 21, wherein trace amounts of the solvent used are detectable by gas chromatography, preferably, the solvents are below ICH limits such as below 5000 ppm for class 3 solvents or even lower for class 1 and class 2 solvents. With regard to the different classes of solvents, reference is made to the disclosure elsewhere herein.

23. The granules according to item 21 or 22, wherein the granules are prepared by a wet granulation process as defined in any of items 9-12.

24. The granules according to item 21 or 22, wherein the granules are prepared by a spray-drying process as defined in any of item 13 and 18.

25. The particles according to item 21, wherein the particles are adsorbates prepared by a process as defined in any of items 15, 16, and 18.

26. Adsorbate comprising afatinib dimaleate on a carrier as defined in item 6 or 7, preferably the carrier is silica.

27. The granules or particles according to any of items 21-25, or the adsorbate according to item 26, wherein the afatinib dimaleate is stable upon storage, such as stable upon storage under stress conditions, for example at 60° C. and 30% humidity for 7 days.

28. The granules or particles or adsorbates according to item 27, wherein the major degradation product Afa-A is present at a level of equal to or less than 3.0%, preferably less than 2.7%, if stored under stress conditions at 60° C. and 30% humidity for 7 days.

29. Process for the preparation of a pharmaceutical composition comprising granules or particles as defined in any one of items 21 to 25 and 27 to 28, or an adsorbate as defined in any of items 26 to 28, comprising:
   a) providing a mixture of the granules or particles, e.g. an adsorbate, and at least one pharmaceutically acceptable excipient;
   b) optionally fine-milling and/or sieving the mixture obtained in step a);
   c) compressing the mixture of step a) or b) into a tablet or filling the mixture into capsules or sachets.

30. Pharmaceutical composition comprising the granules or particles of any one of items 21 to 25 or 27 and 28, or an adsorbate of any of items 26 to 28, and one or more additional pharmaceutically acceptable excipient(s).

31. The pharmaceutical composition according to item 30, wherein the pharmaceutical composition is a compressed dosage form, preferably an oral dosage dosage form such as a solid oral dosage form, more preferably the pharmaceutical composition is a tablet.

32. The pharmaceutical composition according to item 30 or 31, wherein said one or more additional pharmaceutically acceptable excipient is selected from the group consisting of fillers, disintegrants, binders, lubricants, glidants, surfactants, wetting agents, film-forming agents and coating materials, sweeteners, flavoring agents, and coloring agents such as pigments.

33. The pharmaceutical composition according to any of items 30 to 32 for use in a method of treating diseases which can be treated by inhibition of tyrosine kinase, such as breast cancer, colorectal cancer, gastrointestinal cancer, genitourinary cancer, glioma, head and neck cancer, lung cancer, NSCLC, prostate cancer, and solid tumor.

BRIEF DESCRIPTION OF THE DRAWINGS

FIG. 1: This FIGURE shows the dissolution properties of the preparations of Examples 5 to 10 and Comparative Example 1.

DETAILED DESCRIPTION OF THE INVENTION

The present invention is now described in more detail by preferred embodiments and examples, which are however presented for illustrative purpose only and shall not be understood as limiting the scope of the present invention in any way.

Within the context of the present invention it has now unexpectedly been found that a process for preparing granules or particles comprising an API that exhibits challenging physical and/or physicochemical characteristics, e.g. being sensitive towards moisture, such as afatinibe dimaleate, comprising the steps of providing afatinib dimaleate and at least one pharmaceutically active excipient; and preparing granules or particles involving the use of at least one solvent selected from the group consisting of organic solvents and water, and wherein all pharmaceutically acceptable excipients which are used are in said process have neutral or acidic properties, represents an improved process for preparing said granules or particles, in particular with regard to the preparation process itself and with regard to the thus-obtained granule and/or particle.

Surprisingly, it has been found in the present invention that the use of a pharmaceutically acceptable excipient that has neutral or acidic properties in the process according to the present invention can result in granules or particles that exhibit an improved stability, e.g. less degradation products occur. Additionally, by applying the inventive process, the obtained granules and particles can exhibit an improved dissolution profile. Additionally, by applying the inventive method, it is even possible to use an aqueous granulation liquid, e.g. water or mixtures of water with organic solvents, or mixtures of organic solvents, for preparing the granules and/or particles and adsorbates.

Without wishing to be bound by any theory, it is believed that by using exclusively pharmaceutically acceptable excipients that have neutral or acidic properties when preparing the granules and/or particles, no (or comparatively less) interaction occurs between the API of the present invention and said pharmaceutically acceptably excipient(s), in particular fillers or carriers. This is contrary to the situation where pharmaceutically acceptable excipients exhibiting basic properties are used: In this case, the API of the present invention undergoes a degradation process, resulting in the formation of a comparably high amount of degradation products that are derived from the API of the present invention. Thus, by using pharmaceutically acceptable excipients that have neutral or acidic properties, such interaction between said excipient(s) and said API are less (or do not occur), thereby resulting in an improved product, which is for instance improved with regard to dissolution properties and/or stability. Degradation can take place during the manufacturing process, where a solvent is present and enhances the degradation process, but also during a later storage of the granules.

The effects provided by the present invention are all the more surprising as several prior art approaches that aimed at improving the properties (e.g. stability properties or dissolution properties) of API that exhibits challenging physical and/or physicochemical characteristics (e.g. afatinib dimaleate) have failed, for instance also because of the occurrence of unwanted interactions between the API and the excipients being used during manufacturing process. Usually, for improvement purposes, such API is recrystallized, or various granulation techniques are applied. However, with regard to said API, in particular afatinib dimaleate, it is known from prior art that wet granulation resulted in hydrolytical decomposition of the API and further degradation processes occurred during processing. For instance hot melt granulation resulted in granules that exhibited disadvantageous properties, e.g. with regard to variations in poured density of the product, or its tendency to form wall-adhesion inside processing tools. Dry granulation resulted e.g. in an unsatisfactorily prolonged disintegration time. Thus, until now it was not possible to simply apply standard prior art techniques by routine in order to provide API (or granules or particles comprising API, respectively) that exhibits on the one hand improved properties with regard to its physical and/or chemical stability, and on the other hand is suitable for robust, fast and cost efficient processing, resulting in the final dosage form.

When preparing intermediates (such as granules and/or particles) for final dosage forms (e.g. tablets or capsules), the API used also has to exhibit adequate formulation characteristics.

In the context of the present invention, it has been found that by applying the inventive process, granules and/or particles can be prepared which exhibit improved characteristics e.g. improved stability, but also with regard to processibility and/or dissolution properties. The granules/particles can be used as intermediates for preparing final dosage forms such as compressed tablets or capsules, or they can be directly filled into sachets.

By applying the inventive process, the segregation of the API for instance inside a powder mixture can be impeded, which is beneficial for reproducible and uniform API content uniformity, e.g. within the batches or among the batches, in particular in low dose formulations or direct compression processes. Additionally, the application of the inventive process can be beneficial with regard to flowability, compressibility, cohesiveness or lubrication of the API, and thus can be beneficial for processibility in automated production processes. For instance, in the production of solid oral dosage forms such as tablets free flow of material into the die is necessary in order to ensure adequate and reproducible solid oral dosage mass, content uniformity, hardness and dissolution profile of said dosage form. Additionally, the inventive process can further be beneficial with regard to cohesiveness in order to keep the compact from crumbling and falling apart from handling. Finally, the inventive process can be beneficial with regard to tablet ejection.

All in all, applying the process according to the present invention results in granules and/or particles that exhibit improved properties e.g. with regard to dissolution or degradation of the API, and/or its formulation characteristics in general.

The present invention thus relates to a process for preparing granules or particles comprising an API exhibiting challenging physical and/or physico-chemical characteristics that are e.g. relevant for processibility in the preparation of dosage forms, in particular afatinib dimaleate, comprising the steps of:
(a) providing said API, preferably afatinib dimaleate, and at least one pharmaceutically acceptable excipient; and
(b) preparing granules or particles by use of said API, preferably afatinib dimaleate, and at least one pharmaceutically acceptable excipient as provided in step (a), and at least one solvent selected from organic solvents or mixtures thereof and water;
wherein all pharmaceutically acceptable excipients which are used in the process for preparing granules or particles have neutral or acidic properties, wherein the excipient is determined to have neutral properties if the pH of a solution/suspension of the excipient in water when measured by pH meter has a pH of 6 to 8, and wherein the excipient is determined to have acidic properties if the pH of the solution/suspension of the excipient in water has a pH of less than 6, and wherein said API as provided in step (a) has a solubility of at least 5 mg/ml in said at least one solvent of step (b).

In other words, according to the invention, no basic excipient is used for preparing granules and particles. However, the extragranular or extraparticulate, respectively, phase of a pharmaceutical composition dosage form can comprise basic excipients. It is also preferred not to include a further API having basic properties into the granules/particles. While more than one API can be used, typically, only one API is present. Thus, in one aspect of the invention, only one API is used, preferably afatinib dimaleate.

In order to determine whether an excipient is acidic, basic or neutral, the following test is applied: An amount of 1-10 g, preferably 5 g, of the test excipient is dissolved/suspended in an amount of 99-90 ml, preferably 95 ml of purified water. The pH of the solution/suspension is measured by using a pH meter. If the pH of the solution/suspension is 6-8 the excipient has neutral properties, below 6 acidic and above 8 it has alkaline properties.

Within the meaning of the present invention, the expression "challenging physical and/or physico-chemical characteristics" denotes an API that exhibits characteristics (or properties, respectively), which are relevant with regard to its processibility. Examples of such characteristics are one or more of the following: susceptibility against moisture affecting the chemical stability of the API; needle shape of the precipitated API, causing a high variation of its poured density due to random arrangement and length of the needles, poor flow properties due to increased resistance of the needles to align flow direction, capping or laminating of solid dosage forms such as tablets during a direct compression process due to entrapment of too much air inside the final blend; low compressibility; adhesive properties of the API on surfaces; a random variability of its poured densities. An example of such API, exhibiting challenging physical and/or physico-chemical characteristics, is afatinib dimaleate. The challenging nature of afatinib dimaleate is for instance described in U.S. Pat. No. 8,545,884 B2. In general, APIs are challenging, if they have similar properties like afatinib dimaleate (needle shaped crystals). It is understood that each API that exhibits the challenging physical and/or physico-chemical characteristics e.g. as denoted above can be subjected to the process according to the present invention. In a preferred embodiment, the API is afatinib dimaleate.

Within the meaning of the present invention, the term "granule" or "granules" denotes the product of a granulation process, e.g. a wet granulation process or a spray drying process which results in aggregates of particles, i.e. the granules. Such granules typically have a size distribution wherein 90 wt.-% of the granules have a size of more than 0.2 mm and 90 wt.-% of the granules have a size of 4.0 mm or less as determined by sieve analysis (determined by using a sieve having a size of 0.2 mm and 4.0 mm, respectively). The size can be controlled, respectively, by adjusting process parameters. Preferred is a size distribution, wherein 90 wt.-% of the granules have a size of more than 0.250 mm and 90 wt.-% of the granules have a size of 0.710 mm or less as determined by sieve analysis (determined by using a sieve having a size of 0.250 mm and 0.710 mm, respectively). Spray dried particles can be very small (e.g. 90 wt.-% have a size of more than 0.001 mm and 90 wt. % have a size of 0.100 mm or less), but are usually further agglomerated into aggregates of bigger diameters, depending on their further use. Further details on how to perform the sieving analysis can be found in the European Pharmacopoeia 8.0, Chapter 2.9.38, "Particle-size distribution estimation by analytical sieving" (01/2010:20938). In particular, the European Pharmacopoeia describes the use of air-jet sieving for the above-described small spray dried particles wherein 90 wt.-% have a size of more than 0.001 mm and 90 wt. % have a size of 0.100 mm or less.

Within the meaning of the present invention, the term "particle" or "particles" denotes e.g. an adsorbate or spray-dried particle and does not refer to agglomerates. In general, the size distribution of particles, and thus also of adsorbates, can be determined by sieve analysis, as indicated above. The adsorbates are predominantly formed by adsorption of API in the pores of the adsorbent. Thus the size of adsorbate particle is practically equal to the size of the adsorbent, e.g. is the size of the silicon dioxide used, such as Syloid XDP6.

According to the present invention, the at least one solvent can be an organic solvent and/or water. Preferably, the at least one solvent is selected from the group consisting of acetone, methanol, ethanol, and 2-propanol, more preferably, the organic solvent is acetone and/or methanol. Further preferred, the solvent is acetone. Organic solvents for use according to the invention typically have a water content of below 1% v/v. It is also possible to use organic solvent as defined herein, in combination with water in different ratios, e.g. 1 to 99% of water, preferably from 1 to 20% of water, with the remainder being organic solvent(s). Further, the solvent used is such that the API, preferably afatinib dimaleate, has a solubility of at least 5 mg/ml in the respective solvent. The solubility of the API in the test solvent can be determined by using the standard solubility determination method. According to this method, API is weighted in excess into flasks containing solvent, e.g. 20 ml. Flasks are shaken at room temperature for 24 hours, undissolved API is removed by filtration or centrifugation. An aliquot of the solution of e.g. 10 ml is withdrawn and subjected to solvent evaporation at reduced pressure. The amount of dissolved API is then determined by weighing.

The solubility of the API in the respectively chosen API, preferably afatinib dimaleate, is at least 5 mg/ml in the solvent used. In a preferred embodiment, if the process for preparing the granules according to the present invention is wet granulation, the API has a solubility of at least 20 mg/ml in the solvent used, preferably at least 25 mg/ml. If the process for preparing the particles is adsorbate formation, the API has a solubility of at least 5 mg/ml in the solvent used, preferably at least 8 mg/ml. If the process used for preparing the granules is spray drying, the API has a solubility of at least 5 mg/ml, preferably at least 8 mg/ml, and if the process used is spray coating, the API has a solubility of at least 5 mg/ml preferably at least 8 mg/ml.

The pharmaceutically acceptable excipient(s) that is (are) used in step (b) of the process of the present invention have neutral or acidic properties. Preferably, the excipient(s) exhibit(s) acidic properties.

The process of the invention can be selected from the group consisting of wet granulation, e.g. fluid bed granulation, spray-coating, spray-drying and adsorbate formation, preferably the process is selected from the group consisting of wet granulation, spray-drying, and adsorbate formation. In one aspect, the invention refers to a wet granulation process for preparing granules comprising afatinib dimaleate, wherein a granulation liquid comprising the at least one solvent, preferably methanol or water, and at least one binder is used. Afatinib dimaleate can be completely dissolved in the granulation liquid. In another aspect, the process is a spray-drying process for preparing granules comprising afatinib dimaleate, wherein a solution comprising afatinib dimaleate, the at least one solvent and optionally at least one binder is subjected to a spray-drying process, wherein preferably polyvinylpyrrolidone and its derivatives, such as Kollidon VA64®, are used as binder.

In one embodiment, the granules or particles of the invention additionally comprise an antioxidant, preferably an antioxidant selected from the group consisting of butylated hydroxytoluene, butylated hydroxyanisole, alpha tocopherol, rosmarinic acid, monothioglycerol, thioglycolic acid, ascorbic acid, dodecyl gallate, propyl gallate, octyl gallate, sodium ascorbate, sodium metabisulfite sodium sulfite, sodium bisulfite, more preferably the antioxidant is butylated hydroxytoluene (BHT).

According to the invention, the at least one binder can be selected from the group consisting of: polymeric cellulose derivatives, such as carboxymethyl cellulose (CMC), hydroxypropyl cellulose (HPC), hydroxyethyl cellulose (HEC) and hydroxypropylmethyl cellulose (HPMC); gelatin; gelatin hydrolysate; sucrose; dextrose; and non-cellulosic binders, such as polyvinylpyrrolidone (PVP), polyethyleneglycol (PEG), vinyl pyrrolidone copolymers, pregelatinized starch, sorbitol, and glucose; and polyacrylates (e.g. Eudragit®), preferably the at least one binder is selected from the consisting of: polyvinylpyrrolidone and its derivatives such as Kollidon; cellulose derivatives such as HPMC; and polyoxyethylene/polyethyleneglycol polymers such as PEG. Preferably, the at least one binder is selected from polyvinylpyrrolidone and its derivatives, such as Kollidon VA64®; cellulose derivatives, such as HPMC; and polyoxyethylene/polyethyleneglycol polymers (e.g. PEG 6000) and/or wherein lactose, sodium starch glycolate or silica is used as a carrier.

In one aspect, afatinib dimaleate is present in the granules or particles in amorphous form. If it is desired to prepare afatinib dimaleate-containing granules or particles in amorphous form, which can provide an improved solubility, it is preferred to prepare said granules or particles in a "solid dispersion" sense. This means that the API is trapped inside a polymer matrix (in dispersed form). Accordingly, a polymeric binder has to be used. Preferred polymeric binders are Kollidon®-type binders (i.e. polyvinylpyrrolidone, binders based on polyvinylpyrrolidone/povidone polymers such as polyvinylpyrrolidone polyvinylacetate copolymers), HPMC (hydroxypropylmethylcellulose), polyethylene glycol or mixtures of the aforementioned. Preferred carriers for preparing solid dispersions are silicon dioxide, lactose croscarmellose sodium, sodium starch glycolate, and crospovidone. One type of silicon dioxide is a Syloid®-type carrier, which is characterized by having a minimum BET surface area of 200 m2/g as determined by ASTM D4567 with nitrogen adsorption with single point calculation. This type of Syloid is preferably used for adsorbates.

In order to prepare solid dispersion, it is required that both the API and the one or more binder(s) is/are dissolved during granulation/particle formation. If the API and binder(s) are used in the form of a solution, a carrier has to be used when applying a wet-granulation, spray-coating process or adsorbate formation process, wherein said carrier remains solid during the process. If a spray-drying process is used, no carrier is required.

Accordingly, irrespective of whether the API shall be in amorphous or crystalline form, the process can comprise the use of at least one carrier having neutral or acidic properties, preferably acidic properties, as determined by the method described herein. As mentioned above, a carrier can be used when applying a wet-granulation, spray-coating process or adsorbate formation process. For spray-coating and adsorbate formation, a carrier is mandatory.

According to the present invention, preferably, the at least one carrier with neutral or acidic properties is selected from the group consisting of lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate, magnesium aluminum silicates, silica, dextrose, silicon dioxide (such as Syloid), croscarmellose sodium, sodium starch glycolate, and crospovidone; preferably the at least one carrier is selected from the group consisting of silicon dioxide, croscarmellose sodium, sodium starch glycolate, and crospovidone.

The preferred carrier in adsorbate formation is silicon dioxide, such as Syolid®. The carrier that is used in adsorbate formation is also referred to herein as "adsorbent".

Preferred binders or preferred carriers or preferred solvents as well as combinations of binders and carriers as well as combinations of solvents, binders and carriers are shown in the below table (embodiment no./solvent/binder/carrier).

TABLE 1

Preferred binders or preferred carriers or preferred solvents as well as combinations of binders and carriers as well as combinations of solvents, binders and carriers

| | | Combination | |
|---|---|---|---|
| Example | Solvent | Binder | Carrier |
| 1 | Water | Kollidon, e.g. PVP-PVA copolymer | Syloid = silicon dioxide (acidic) |
| 2 | Water | HPMC | Syloid (acidic) |
| 3 | methanol | Kollidon, e.g. PVP-PVA copolymer + PEG 6000 | Syloid (acidic) |
| 4 | methanol | Kollidon, e.g. PVP-PVA copolymer + PEG 6000 | Syloid (acidic) (BHT as antioxidants) |
| 5 | methanol | Kollidon, e.g. PVP-PVA copolymer | Lactose (neutral) |
| 6 | methanol | Kollidon, e.g. PVP-PVA copolymer | Sodium starch glycolate (acidic to neutral) |
| 7 | methanol | Kollidon, e.g. PVP-PVA copolymer + PEG 6000 | Syloid (acidic |
| 8 | Water | / | / |
| 9 | acetone | / | Syloid (acidic) |
| 10 | water | Kollidon, e.g. PVP-PVA copolymer | / |

The following weight ratios for the API and binder are preferred:

Wet granulation: API/binder=100/1 to 1/10, for solid dispersion: 1/1 to 1/10.

Spray-drying: 10/1 to 1/10

Adsorbate formation: 1/1 to 1/100.

Spray-coating: 10/1 to 1/10

In one aspect, the process is for preparing an adsorbate comprising afatinib dimaleate on a carrier, comprising:
i) combining a solution comprising afatinib dimaleate and the at least one solvent with the at least one carrier;
ii) removing the solvent or mixture of solvents under reduced pressure to form the adsorbate.

The pressure applied in step ii) can be from 1 to 350 mbar, preferably from 20 to 250 mbar. One preferred carrier is silica.

The present invention also refers to granules or particles comprising afatinib dimaleate prepared by a process of the invention, preferably granules or particles comprising afatinib dimaleate as a solid dispersion. In one embodiment, the granules are prepared by a wet granulation-, spray-drying- or adsorbate formation-process of the invention. The adsorbate formation process results in an adsorbate comprising afatinib dimaleate on a carrier.

In one aspect, the granules, or particles according to the invention is stable upon storage, optionally upon storage under stress conditions, for example at 60° C. and 30% humidity for 7 days. Preferably, the major degradation product Afa-A is present at a level of equal to or less than 3.0%, preferably less than 2.7%, if stored under stress conditions at 60° C. and 30% humidity for 7 days. The amount of the main impurity, which is a result of hydrolytic cyclization of afatinib, i.e. the degradation product afatinib A (Afa-A), can be determined by chromatographic purity.

General protocol for determining the degradation product Afa-A is as follows:
1. Weigh an appropriate amount of the powder into a volumetric flask.
2. Add diluent to about half of the flask and shake on a mechanical shaker for prescribed period.
3. Dilute to volume with diluent, mix well and filter the solution.
4. Inject the sample solutions into the chromatograph and measure the responses for the major peaks.

Afa-A has the following chemical structure:

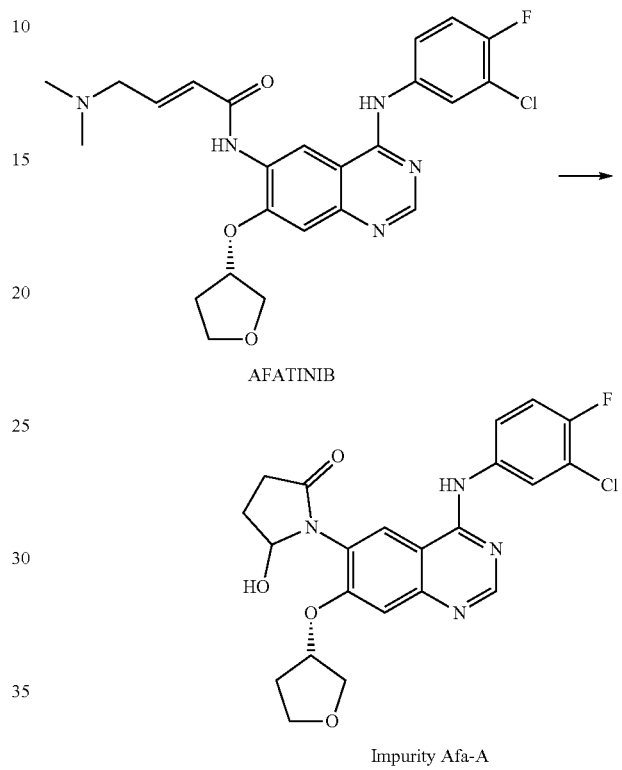

AFATINIB

Impurity Afa-A

The granules or particles may only contain trace amounts of solvent(s) that are preferably in accordance with ICH (see below) limits for residual solvents, e.g. below 5000 ppm for class 3 solvents or even lower for class 1 and class 2 solvents as determined by gas chromatography.

The limits and definition and examples of class 1, 2, and 3 solvents can be found in the "ICH Harmonised Tripartite Guideline; Impurities: Guideline For Residual Solvents, Q3C (R5), Current Step 4 version dated February 2011" and are defined as follows: Class 1 solvents are solvents to be avoided. Class 1 solvents are defined as known human carcinogens, strongly suspected human carcinogens, and environmental hazards. Class 1 solvents should not be employed in the manufacture of drug substances, excipients, and drug products, e.g. because of their toxicity.

Class 2 solvents are solvents to be limited, and are defined as non-genotoxic animal carcinogens or possible causative agents of other irreversible toxicity such as neurotoxicity or teratogenicity. Further class 2 solvents are solvents suspected of other significant but reversible toxicities. Class 2 solvents should be limited in pharmaceutical products because of their inherent toxicity.

Class 3 solvents are solvents with low toxic potential and are defined as solvents with low toxic potential to man: no health-based exposure limit is needed. Class 3 solvents have permitted daily exposures (PDEs) of 50 mg or more per day. Solvents of class 3 may be regarded as less toxic and of lower risk to human health.

The present invention further refers to a process for preparing a pharmaceutical composition comprising an API exhibiting challenging physical and/or physico-chemical characteristics relevant for processibility in the preparation of pharmaceutical compositions such as dosage forms, in particular afatinib dimaleate, comprising the steps of:

(A) carrying out a process for preparing granules or particles according to the invention;
(B) mixing the prepared granules or particles comprising said API, in particular afatinib dimaleate, with one or more additional pharmaceutically acceptable excipients.

Said one or more additional pharmaceutically acceptable excipient can be selected from the group consisting of fillers, disintegrants, binders, lubricants, glidants, surfactants, wetting agents, film-forming agents and coating materials, sweeteners, flavoring agents, and coloring agents. In a preferred embodiment, said one or more additional pharmaceutically acceptable excipients have neutral or acidic properties, as determined by the method indicated elsewhere herein.

The invention also refers to a process for the preparation of a pharmaceutical composition comprising granules or particles, preferably an adsorbate, of the invention, comprising:

a) providing a mixture of the granules, particles, preferably an adsorbate, and at least one additional pharmaceutically acceptable excipient;
b) optionally fine-milling and/or sieving the mixture obtained in step a);
c) compressing the mixture of step a) or b) into a tablet or filling the mixture into capsules or sachets.

Thus, the granules or particles prepared according to the present invention can be considered as "intermediate products" that are further used in preparing a pharmaceutical composition, preferably a final dosage form such as a solid oral dosage form.

The invention thus refers to a pharmaceutical composition comprising the granules or particles of the invention and one or more additional pharmaceutically acceptable excipients. The pharmaceutical composition can be a compressed dosage form, preferably a tablet.

Said one or more additional pharmaceutically acceptable excipient can be selected from the group consisting of fillers, disintegrants, binders, lubricants, glidants, surfactants, wetting agents, film-forming agents and coating materials, sweeteners, flavoring agents, and coloring agents such as example pigments. Preferably, said pharmaceutically acceptable excipients have neutral or acidic, preferably acidic, properties. Such properties can be determined as disclosed elsewhere herein. Further, said preferred pharmaceutically acceptable excipients having neutral or acidic properties are as disclosed elsewhere herein.

The pharmaceutical composition, granules and particles of the invention can be used in a method of treating diseases which can be treated by inhibition of tyrosine kinase, such as breast cancer, colorectal cancer, gastrointestinal cancer, genitourinary cancer, glioma, head and neck cancer, lung cancer, NSCLC, prostate cancer, and solid tumor.

EXAMPLES

In the examples, afatinib dimaleate was used as API.

Comparative Example 1: Dry Granulation

As a reference product, "Giotrif®" tablets 50 mg available in the European Union, batch no. 305921, exp. date July 2016, have been used. The inventors presently assume that these Giotrif® tablets have been prepared as described in U.S. Pat. No. 8,545,884 B2, in particular as disclosed in col. 15, starting from line 53, to col. 17, l. 55 therein, and that Giotrif 50 mg corresponds to Formulation D as disclosed in col. 24.

The inventors have qualitatively analyzed the Giotrif tablet: The tablet comprises: afatinib dimaleate, lactose monohydrate, cellulose microcrystalline, silica colloidal anhydrous, crospovidone and magnesium stearate. Tablet cores are further coated with standard nonfunctional water based coating.

The reference product Giotrif releases 100% of API in 20 minutes as determined by use of an Apparatus 2 (paddle) described in European Pharmacopoeia 6.2. The following conditions were applied:

Apparatus 2 (paddle)
Paddle speed: 75 rpm
Dissolution medium: McIlvaine Buffer pH 4.0
Volume: 900 ml
Sampling time point: 5, 10, 15, 20, 30, 45, 60 min The same dissolution test was applied in the examples below.

Additionally, the reference product Giotrif was exposed to stress test of 60° C./RH 30% for 7 days to assess chemical stability of the product.

Then, the reference product Giotrif was analyzed for impurities and one major degradation product ("Afa-A") was detected in the level of 1.96%.

Using NMR experiments the chemical structure of the main impurity Afa-A (see below), which is a result of hydrolytic cyclization of Afatinib, could be determined:

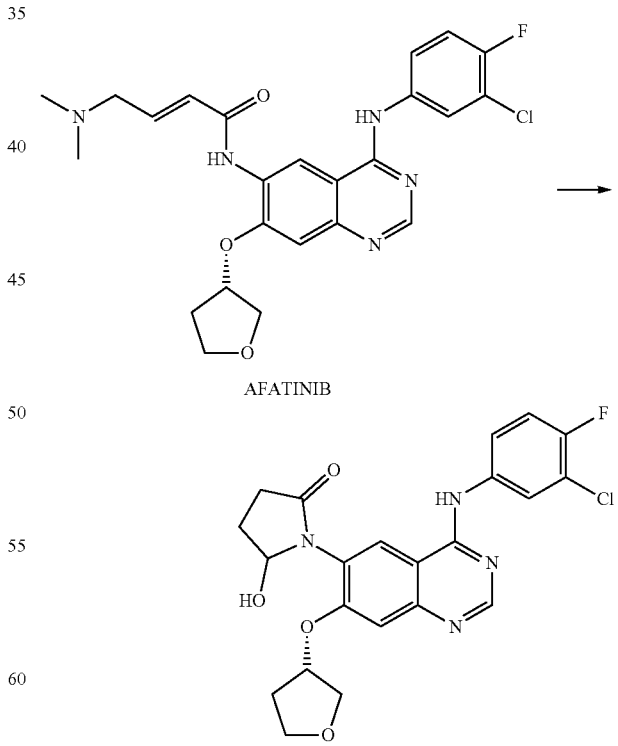

According to Australian Public Assessment Report for afatinib ("Giotrif"; April 2014), the level of this main impurity (called "CD 334" in the report; page 9 therein) in the tablet is registered at levels of ≤3.0%.

Therefore, stress test of 60° C./RH 30% for 7 days represents a good predictive tool for long-term stability.

The following examples (Example 1 to 10) inter alia show that a chemically stable afatinib dimaleate granulate can be prepared using wet granulation and water as granulation liquid. This is contrary to the general teaching and understanding as it is for instance reflected in U.S. Pat. No. 8,545,884 B2. According to U.S. Pat. No. 8,545,884 B2, "Wet granulation was not suitable, as the API underwent hydrolytical decomposition and further degradation reaction during processing". API was in amorphous state. It is assumed that if a stable granulate can be prepared, a preparation of stable FDF ("Finished Dosage Form") is also possible.

Example 1 (015X1): Wet Granulation

In this example, Kollidon VA64® was used as binder and water as granulation liquid.

Kollidon VA64® (4 g) was dissolved in water until clear solution was obtained. Afatinib dimaleate (2 g) was added and the solution was mixed until a clear solution was obtained. Syloid FP244 (8 g) was used as carrier. The solution of afatinib dimaleate was used to granulate the carrier. The resulting wet granulate was dried.

The resulting dry granulate was exposed to stress stability.

|  | 7 days<br>60° C./30% RH |
|---|---|
| Level of impurity Afa-A | 1.79% |
| Form | amorphous |

The example shows that preparation of intermediates (granulate) with wet granulation using aqueous media is possible. API can also even be in amorphous state (more susceptible to degradation) and still the stress stability results are within the reference stability requirements.

Example 2 (018X1): Wet Granulation

In this example, HPMC was used as binder and water as granulation liquid.

Hydroxypropyl methylcellulose (4 g) was dissolved in water until clear solution was obtained. Afatinib dimaleate (2 g) was added and the solution was mixed until a clear solution was obtained. Syloid FP244 (8 g) was used as carrier. The solution of afatinib dimaleate was used to granulate the carrier. The resulting wet granulate was dried.

The resulting dry granulate was exposed to stress stability.

|  | 7 days<br>60° C./30% RH |
|---|---|
| Level of impurity Afa-A | 1.62% |
| Form | amorphous |

The example shows results similar to Example 1.

Example 3 (001Y1): Wet Granulation

In this example Kollidon VA64® and PEG 6000 were used as binders and methanol as granulation liquid.

Kollidon VA64® (0.5 g) and PEG 6000 (0.5 g) were dissolved in methanol until a clear solution was obtained. Afatinib dimaleate (0.5 g) was added and the solution was mixed until a clear solution was obtained. Syloid FP244 (2 g) was used as carrier. The solution of afatinib dimaleate was used to granulate the carrier. The resulting wet granulate was dried.

The resulting dry granulate was exposed to stress stability.

|  | 7 days<br>60° C./30% RH |
|---|---|
| Level of impurity Afa-A | 2.53% |
| Total impurities | 10.57% |
| Form | amorphous |

The example shows that preparation of FDF (Finished Dosage Form) with wet granulation using organic media for preparation of intermediates is possible.

Example 4 (001Y2): Wet Granulation

In this example Kollidon VA64® and PEG 6000 were used as binders, butylated hydroxytoluene as antioxidant, and methanol as granulation liquid.

Kollidon VA64® (0.5 g), PEG 6000 (0.5 g) and butylated hydroxytoluene (0.001 g) were dissolved in methanol until a clear solution was obtained. Afatinib dimaleate (0.5 g) was added and the solution was mixed until a clear solution was obtained. Syloid FP244 (2 g) was used as carrier. The solution of afatinib dimaleate was used to granulate the carrier. The resulting wet granulate was dried.

The resulting dry granulate was exposed to stress stability.

|  | 7 days<br>60° C./30% RH |
|---|---|
| Level of impurity Afa-A | 1.99% |
| Total impurities | 3.57% |
| Form | amorphous |

The example shows that preparation of FDF with wet granulation using organic media for preparation of intermediates is possible. And API stability can be improved by addition of antioxidants (compare to example 3).

Example 5 (004X): Wet Granulation

In this example, Kollidon VA64® was used as binder and methanol as granulation liquid.

Kollidon VA64® (4 g) was dissolved in methanol until clear solution was obtained. Afatinib dimaleate (2 g) was added and the solution was mixed until a clear solution was obtained. Lactose (8 g) was used as carrier. The solution of afatinib dimaleate was used to granulate the carrier. The resulting wet granulate was dried. Afatinib dimaleate in the granules was in amorphous form.

The granulate (5 g) was mixed with colloidal silicon dioxide (0.0753 g), croscarmellose sodium (0.169 g) and magnesium stearate (0.0753 g). The resulting mixture was compressed into tablets.

Tablet releases below 70% of API in 20 minutes in a standard release media (see FIG. 1).

This example shows that an afatinib dimaleate FDF can be prepared using wet granulation and methanol as granulation liquid.

Example 6 (022X): Wet Granulation

In this example, Kollidon VA64® was used as binder and methanol as granulation liquid.

Kollidon VA64® (4 g) was dissolved in methanol until clear solution was obtained. Afatinib dimaleate (2 g) was added and the solution was mixed until a clear solution was obtained. Sodium starch glycolate (8 g) was used as carrier. The solution of afatinib dimaleate was used to granulate the carrier. The resulting wet granulate was dried. Afatinib dimaleate in the granules was in amorphous form.

The granulate (1.474 g) was mixed with mannitol (0.416 g), croscarmellose sodium (0.084 g), colloidal silicon dioxide (0.005 g) and magnesium stearate (0.021 g). The resulting mixture was compressed into tablets.

Tablet releases 82% of API in 20 minutes in a standard release media (see FIG. 1).

Example 7 (027X1): Wet Granulation

In this example, Kollidon VA64® and PEG 6000 were used as binder and methanol as granulation liquid.

Kollidon VA64® (0.125 g) and PEG 6000 (0.125 g) were dissolved in methanol until a clear solution was obtained. Afatinib dimaleate (0.2 g) was added and the solution was mixed until a clear solution was obtained. Syloid FP244 (0.8 g) was used as carrier. The solution of afatinib dimaleate was used to granulate the carrier. The resulting wet granulate was dried. Afatinib dimaleate in the granules was in amorphous form.

The granulate (0.737 g) was mixed with mannitol (0.208 g), croscarmellose sodium (0.042 g), colloidal silicon dioxide (0.003 g) and magnesium stearate (0.01 g). The resulting mixture was compressed into tablets.

Tablet releases 100% of API in 20 minutes in a standard release media (see FIG. 1).

Example 8 (031X1 032X1): Wet Granulation

In this example, PVP was used as binder and water as granulation liquid.

Polyvinylpyrrolidone (0.3 g) was dissolved in water. Afatinib dimaleate (2.596 g) was mixed with lactose (12.086) and the mixture was granulated by addition of polyvinylpyrrolidone solution. The resulting wet granulate was dried. Afatinib dimaleate in the granules was in crystalline form.

The resulting dry granulate was exposed to stress stability.

|  | 7 days 60° C./30% RH |
| --- | --- |
| Level of impurity Afa-A | 0.95% |
| Form | crystalline |

Afatinib dimaleate granulate (3.835 g) was mixed with microcrystalline cellulose (0.462 g), crospovidone (0.09 g), colloidal silicon dioxide (0.023 g) and magnesium stearate (0.09 g). The resulting free flowing mixture was compressed into tablets.

Tablet releases 98% of API in 20 minutes in a standard release media (see FIG. 1).

The resulting tablets were exposed to stress stability.

|  | 7 days 60° C./30% RH |
| --- | --- |
| Level of impurity Afa-A | 1.82% |
| Form | crystalline |

The example shows that preparation of FDF with composition similar to the reference is possible even when aqueous media is used for wet granulation.

Example 9 (033X1 and AFTN-ADS-SYL-30/240315): Adsorbates

In this example, acetone was used as solvent.

3 g of afatinib dimaleate was dissolved in 30 ml of acetone and in portion added to 10 g of Syloid XDP6. In between and at the end the mixture was dried under reduced pressure at 50° C. The product was amorphous which was confirmed by X-Ray Powder Diffraction using a copper K-alpha anode wavelength of 0.15418 nm, wherein the product shows a broad halo with no diffraction peaks present.

Afatinib dimaleate adsorbate was mixed with lactose, hydroxypropyl cellulose, crospovidone and magnesium stearate. The resulting free flowing mixture was compressed into tablets.

FDF releases 95% of API in 20 minutes in a standard release media (see FIG. 1).

The resulting tablets and intermediate (adsorbate) were exposed to stress stability.

|  | 7 days 60° C./30% RH | |
| --- | --- | --- |
| Sample type | adsorbate | tablet |
| Level of impurity Afa-A | 1.39% | 2.14% |
| Form | amorphous | amorphous |

The example shows that preparation of FDF with adsorbate intermediates is possible. API can also even be in amorphous state (more susceptible to degradation) and still the stress stability results are within the reference stability requirements.

Example 10 (013X1): Spray Drying

In this example, Kollidon VA64® was used as binder and water as granulation liquid.

Kollidon VA64® (4 g) was dissolved in water until clear solution was obtained. Afatinib dimaleate (1 g) was added and the solution was mixed until a clear solution was obtained. The resulting solution was spray dried to prepare a dry granulate. The resulting granulate (1.168 g) was mixed with mannitol (0.722 g), croscarmellose sodium (0.084 g), colloidal silicon dioxide (0.005 g) and magnesium stearate (0.021 g). The resulting free flowing mixture was compressed into tablets.

FDF releases 76% of API in 20 minutes in a standard release media (see FIG. 1).

The resulting tablets were exposed to stress stability.

|  | 7 days<br>60° C./30% RH |
| --- | --- |
| Level of impurity Afa-A | 2.68% |
| Form | amorphous |

The example shows that preparation of FDF with spray dried intermediates is possible. API can also even be in amorphous state (more susceptible to degradation) and still the stress stability results are close to reference stability requirements.

Methods of Analysis:

Solid state form was determined by X-Ray powder diffraction method:

The powder X-ray diffraction patterns were obtained by methods known in the art using PANalytical X'Pert PRO diffractometer with X'Celerator detector using CuKα radiation (tube operating at 45 kV and 40 mA) in the Bragg-Brentano (reflection) geometry. Data were recorded from 2 to 40 ° 2θ in steps of 0.033 ° 2θ and the measurement time of 50 seconds per step. Variable divergence and antiscatter slits were used to maintain 10 mm of sample length irradiated.

Level of Afa-A impurity was determined by HPLC and UPLC analytical methods:

In HPLC method, XBridge C18 2.5 μm (4.6×75) mm column with flow rate of 2 ml/min at 40° C. was used. A gradient elution from 5 to 60% of mobile phase B was applied. Mobile phase A was constituted from 95% of 10 mM $NaH_2PO_4$ (pH 3) and 5% of acetonitrile. Mobile phase B was 100% acetonitrile. Absorbance chromatograms were recorded at 265 nm.

In UPLC method, CSH C18 1.7 μm (2.1×100) mm column with flow rate of 0.6 ml/min at 60° C. was used. A gradient elution from 7 to 70% of mobile phase B was applied. Mobile phase A was 0.1% formic acid (pH 2.85. Mobile phase B constituted from 65% acetonitrile and 35% methanol. Absorbance chromatograms were recorded at 265 nm.

The invention claimed is:

1. Process for preparing amorphous granules or particles comprising afatinib dimaleate, wherein the process comprises:
    (a) providing afatinib dimaleate and at least one pharmaceutically acceptable excipient; and
    (b) preparing amorphous granules or particles by use of afatinib dimaleate and at least one pharmaceutically acceptable excipient as provided in step (a), and at least one solvent selected from organic solvents and water;
    wherein all pharmaceutically acceptable excipients which are used in the process for preparing granules or particles have neutral or acidic properties,
    wherein the excipient is determined to have neutral properties if the pH of a solution/suspension of the excipient in water when measured by pH meter has a pH of 6 to 8, and
    wherein the excipient is determined to have acidic properties if the pH of the solution/suspension of the excipient in water has a pH of less than 6, and
    wherein said afatinib dimaleate as provided in step (a) has a solubility of at least 5 mg/ml in said at least one solvent of step (b).

2. The process according to claim 1, wherein the at least one solvent is an organic solvent.

3. The process according to claim 1, which is selected from the group consisting of wet granulation, spray-coating, spray-drying and adsorbate formation.

4. The process according to claim 1, comprising the use of at least one carrier, wherein said at least one carrier has neutral or acidic properties as determined by the method indicated in claim 1.

5. The process according to claim 1, which is a wet granulation process for preparing granules comprising afatinib dimaleate, wherein a granulation liquid comprising the at least one solvent and at least one granulation binder, is used.

6. The process according to claim 1, which is a spray-drying process for preparing granules comprising afatinib dimaleate, wherein a solution comprising afatinib dimaleate, the at least one solvent and optionally at least one binder is subjected to a spray-drying process.

7. The process according to claim 1 which is a process for preparing an adsorbate comprising afatinib dimaleate on a carrier, comprising:
    i) combining a solution comprising afatinib dimaleate and the at least one solvent with the at least one carrier;
    ii) removing the solvent or mixture of solvents under reduced pressure to form the adsorbate.

8. The process according to claim 7, wherein the carrier is silica, and/or wherein the solvent is acetone.

9. Process for preparing a pharmaceutical composition comprising afatinib dimaleate, comprising the steps of:
    (A) carrying out a process according to claim 1; and
    (B) mixing the prepared granules or particles comprising afatinib dimaleate with one or more additional pharmaceutically acceptable excipients.

10. Granules or particles comprising afatinib dimaleate, wherein the granules or particles are present in amorphous form and prepared by a process as defined in claim 1.

11. The granules or particles according to claim 10, wherein the granules are prepared by a wet granulation process, or by a spray-drying process, or wherein the particles are adsorbates.

12. Adsorbate comprising afatinib dimaleate on a carrier as defined in claim 4.

13. The granules or particles according to claim 10, wherein the afatinib dimaleate is stable upon storage.

14. Process for the preparation of a pharmaceutical composition comprising granules or particles as defined in claim 10, comprising:
    a) providing a mixture of the granules or particles, and at least one pharmaceutically acceptable excipient;
    b) optionally fine-milling and/or sieving the mixture obtained in step a);
    c) compressing the mixture of step a) or b) into a tablet or filling the mixture into capsules or sachets.

15. Pharmaceutical composition comprising the granules or particles of claim 10, and one or more additional pharmaceutically acceptable excipients.

16. The pharmaceutical composition according to claim 15 for use in a method of treating diseases which can be treated by inhibition of tyrosine kinase.

* * * * *